(12) United States Patent
Akahoshi et al.

(10) Patent No.: US 8,247,643 B2
(45) Date of Patent: Aug. 21, 2012

(54) GENETICALLY MODIFIED ANIMAL FOR USE IN EVALUATING HARMFULNESS OF TEST SUBSTANCE

(75) Inventors: Eiichi Akahoshi, Tokyo (JP); Mitsuko Ishihara, Tokyo (JP); Tomoyuki Shishido, Ikoma (JP); Shigehisa Kawata, Ikoma (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 267 days.

(21) Appl. No.: 12/559,303

(22) Filed: Sep. 14, 2009

(65) Prior Publication Data

US 2010/0132057 A1 May 27, 2010

(30) Foreign Application Priority Data

Sep. 24, 2008 (JP) .................. 2008-244392

(51) Int. Cl.
*A01K 67/027* (2006.01)
*C07H 21/04* (2006.01)
(52) U.S. Cl. ........................ 800/14; 536/24.1
(58) Field of Classification Search .................... 800/14; 536/24.1
See application file for complete search history.

(56) References Cited

U.S. PATENT DOCUMENTS

| 5,591,626 A | * | 1/1997 | Chikaraishi | 435/354 |
| 2002/0106794 A1 | * | 8/2002 | Iacovitti et al. | 435/368 |
| 2008/0003596 A1 | | 1/2008 | Akahoshi et al. | |

FOREIGN PATENT DOCUMENTS

| JP | 2001-8577 | 1/2001 |
| JP | 2001-8578 | 1/2001 |
| JP | 2002-253231 | 9/2002 |
| JP | 2007-202555 | 8/2007 |

OTHER PUBLICATIONS

Akahashi et al, Environmental Health 8:24, pp. 1-11, 2009.*
Liu et al, AF014956.1; 2000.*
Morgan et al, J. Neuochem. 66(1):20-25, 1996.*
DiLella et al, N.A.R. 16(9):4159, 1988.*

* cited by examiner

*Primary Examiner* — Kevin K. Hill
(74) *Attorney, Agent, or Firm* — Oblon, Spivak, McClelland, Maier & Neustadt, L.L.P.

(57) ABSTRACT

A genetically modified animal that includes an introduced DNA including a functionally linked aryl hydrocarbon receptor-binding enhancer located 5'-upstream of a tyrosine hydroxylase gene, promoter of any type, reporter gene, and poly(A) addition signal.

14 Claims, 5 Drawing Sheets

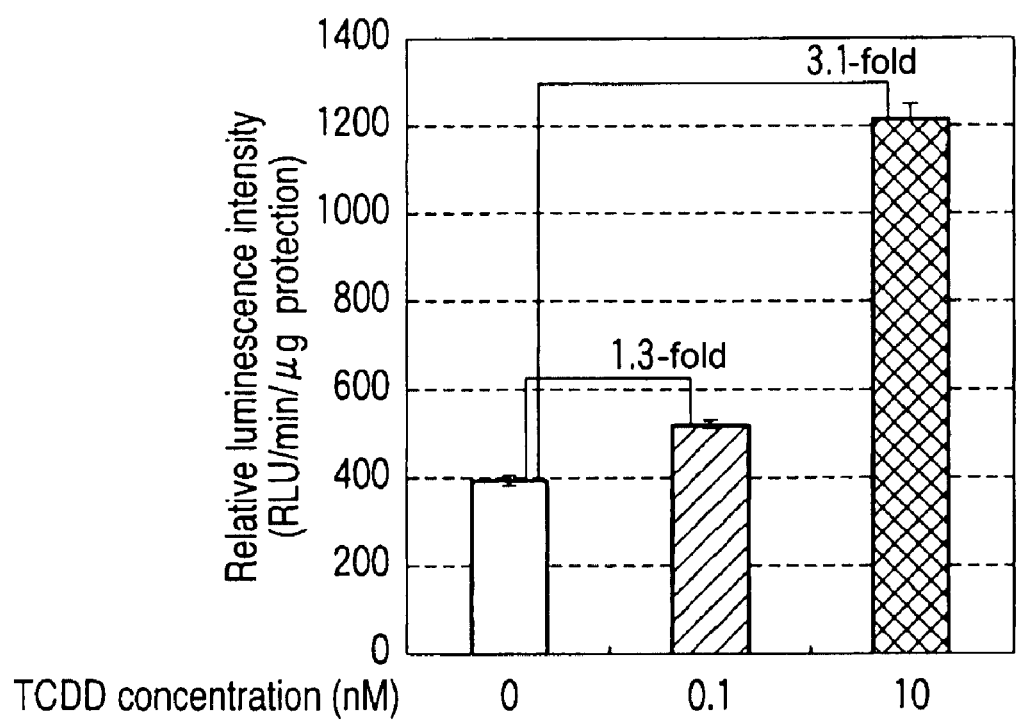
F I G. 9

SEQUENCE LISTING

<160> NUMBER OF SEQ ID NOS: 17

<210> SEQ ID NO 1
<211> LENGTH: 24
<212> TYPE: DNA
<213> ORGANISM: Mus musculus
<220> FEATURE:
<223> OTHER INFORMATION: AhR binding enhancer sequence located in 5'
      upstream region of TH gene coating region

<400> SEQUENCE: 1
gtcttcatgt cgtgtctagg gcgg                                          24

<210> SEQ ID NO 2
<211> LENGTH: 63
<212> TYPE: DNA
<213> ORGANISM: Artificial
<220> FEATURE:
<223> OTHER INFORMATION: Enhancer region derived from mouse TH gene

<400> SEQUENCE: 2
gtcttcatgt cgtgtctagg gcggagggtg attcagaggc aggtgcctgc gacagtggat   60
gca                                                                 63

<210> SEQ ID NO 3
<211> LENGTH: 435
<212> TYPE: DNA
<213> ORGANISM: Artificial
<220> FEATURE:
<223> OTHER INFORMATION: TH gene enhancer region

<400> SEQUENCE: 3
tagatctaat tgcatccact tcgcaggcac ctcctctgaa tcaccctccg ccctagacac   60
gacatgaaga ctgcatccac tgtcgcaggc acctgcctct gaatcaccct ccgccctaga  120
cacgacatga agacaggggc tggcgccagc ccctgtcttc atgtcgtgtc tagggcggag  180
ggtgattcag aggcaggtgc ctgcgacagt ggatgcagtc ttcatgtcgt gtctagggcg  240
gagggtgatt cagaggaggt gcctgcgaca gtggatgcaa ttagatctag ccagcccctg  300
tcttcatgtc gtgtctaggg cggagggtga ttcagaggca ggtgcctgcg acagtggatg  360
cagtcttcat gtcgtgtcta gggcggaggg tgattcagag gcaggtgcct gcgacagtgg  420
atgcaattag atcta                                                   435

<210> SEQ ID NO 4
<211> LENGTH: 95
<212> TYPE: DNA
<213> ORGANISM: Artificial
<220> FEATURE:
<223> OTHER INFORMATION: Promoter of TH gene

<400> SEQUENCE: 4
gtgggggacc cagagggget ttgacgtcag cctggccttt aagaggccgc ctgcctggca   60
agggctgtgg agacagaact cgggaccacc agctt                              95

<210> SEQ ID NO 5
<211> LENGTH: 539
<212> TYPE: DNA
<213> ORGANISM: Artificial
<220> FEATURE:
<223> OTHER INFORMATION: AhR binding enhancer, and promoter of TH gene

<400> SEQUENCE: 5

```
tagatctaat tgcatccact tcgcaggcac ctcctctgaa tcaccctccg ccctagacac     60
gacatgaaga ctgcatccac tgtcgcaggc acctgcctct gaatcaccct ccgccctaga    120
cacgacatga agacaggggc tggcgccagc ccctgtcttc atgtcgtgtc tagggcggag    180
ggtgattcag aggcaggtgc ctgcgacagt ggatgcagtc ttcatgtcgt gtctagggcg    240
gagggtgatt cagaggaggt gcctgcgaca gtggatgcaa ttagatctag ccagcccctg    300
tcttcatgtc gtgtctaggg cggagggtga ttcagaggca ggtgcctgcg acagtggatg    360
cagtcttcat gtcgtgtcta gggcggaggg tgattcagag gcaggtgcct gcgacagtgg    420
atgcaattag atctagggct cgaggtgggg acccagagg  ggctttgacg tcagcctggc    480
ctttaagagg ccgcctgcct ggcaagggct gtggagacag aactcgggac caccagctt    539
```

<210> SEQ ID NO 6
<211> LENGTH: 2507
<212> TYPE: DNA
<213> ORGANISM: Artificial
<220> FEATURE:
<223> OTHER INFORMATION: AhR binding enhancer, TH gene promoter,
      c-myc tag luciferase gene and late poly A signal of SV40 virus

<400> SEQUENCE: 6

```
tagatctaat tgcatccact tcgcaggcac ctcctctgaa tcaccctccg ccctagacac     60
gacatgaaga ctgcatccac tgtcgcaggc acctgcctct gaatcaccct ccgccctaga    120
cacgacatga agacaggggc tggcgccagc ccctgtcttc atgtcgtgtc tagggcggag    180
ggtgattcag aggcaggtgc ctgcgacagt ggatgcagtc ttcatgtcgt gtctagggcg    240
gagggtgatt cagaggaggt gcctgcgaca gtggatgcaa ttagatctag ccagcccctg    300
tcttcatgtc gtgtctaggg cggagggtga ttcagaggca ggtgcctgcg acagtggatg    360
cagtcttcat gtcgtgtcta gggcggaggg tgattcagag gcaggtgcct gcgacagtgg    420
atgcaattag atctagggct cgaggtgggg acccagagg  ggctttgacg tcagcctggc    480
ctttaagagg ccgcctgcct ggcaagggct gtggagacag aactcgggac caccagctta    540
agcttatcat ggagcagaaa ctcatctctg aagaagatct ggcccgggcg tccatggaag    600
acgccaaaaa cataaagaaa ggcccggcgc cattctatcc gctggaagat ggaaagatgg    660
aaccgctgga gagcaactgc ataaggctat gaagagatac gccctggttc ctggaacaat    720
tgcttttaca gatgcacata tcgaggtgga catcacttac gctgagtact cgaaatgtc     780 cgttcggttg gcagaagcta tgaaacgata tgggctgaat acaaatcaca gaatcgtcgt    840
atgcagtgaa aactctcttc aattctttat gccggtgttg ggcgcgttat ttatcggagt    900
tgcagttgcg cccgcgaacg acatttataa tgaacgtgaa ttgctcaaca gtatgggcat    960
ttcgcagcct accgtggtgt tcgtttccaa aaaggggttg caaaaaattt tgaacgtgca   1020
aaaaaagctc ccaatcatcc aaaaaattat tatcatggat tctaaaacgg attaccaggg   1080
atttcagtcg atgtacacgt tcgtcacatc tcatctacct cccggtttta atgaatacga   1140
ttttgtgcca gagtccttcg atagggacaa gacaattgca ctgatcatga actcctctgg   1200
atctactggt ctgcctaaag gtgtcgctct gcctcataga actgcctgcg tgagattctc   1260
gcatgccaga gatcctattt ttggcaatca aatcattccg gatactgcga ttttaagtgt   1320
tgttccattc catcacggtt ttggaatgtt tactacactc ggatatttga tatgtggatt   1380
tcgagtcgtc ttaatgtata gatttgaaga agagctgttt ctgaggagcc ttcaggatta   1440
caagattcaa agtgcgctgc tggtgccaac cctattctcc ttcttcgcca aaagcactct   1500
```

-continued

```
gattgacaaa tacgatttat ctaatttaca cgaaattgct tctggtggcg ctcccctctc    1560
taaggaagtc ggggaagcgg ttgccaagag gttccatctg ccaggtatca ggcaaggata    1620
tgggctcact gagactacat cagctattct gattacaccc gaggggatg ataaaccggg     1680 cgcggtcggt aaagttgttc cattttttga agcgaaggtt gtggatctgg ataccgggaa    1740
aacgctgggc gttaatcaaa gaggcgaact gtgtgtgaga ggtcctatga ttatgtccgg    1800
ttatgtaaac aatccggaag cgaccaacgc cttgattgac aaggatggat ggctacattc    1860
tggagacata gcttactggg acgaagacga acacttcttc atcgttgacc gcctgaagtc    1920
tctgattaag tacaaaggct atcaggtggc tcccgctgaa ttggaatcca tcttgctcca    1980
acaccccaac atcttcgacg caggtgtcgc aggtcttccc gacgatgacg ccggtgaact    2040
tcccgccgcc gttgttgttt tggagcacgg aaagacgatg acggaaaaag agatcgtgga    2100
ttacgtcgcc agtcaagtaa caaccgcgaa aaagttgcgc ggaggagttg tgtttgtgga    2160
cgaagtaccg aaaggtctta ccggaaaact cgacgcaaga aaaatcagag agatcctcat    2220
aaaggccaag aagggcggaa agatcgccgt gtaattctag agtcggggcg gccggccgct    2280
tcgagcagac atgataagat acattgatga gtttggacaa accacaacta gaatgcagtg    2340
aaaaaaatgc tttatttgtg aaatttgtga tgctattgct ttatttgtaa ccattataag    2400
ctgcaataaa caagttaaca acaacaattg cattcatttt atgtttcagg ttcaggggga    2460
ggtgtgggag gttttttaaa gcaagtaaaa cctctacaaa tgtggta               2507
```

<210> SEQ ID NO 7
<211> LENGTH: 1661
<212> TYPE: DNA
<213> ORGANISM: Artificial
<220> FEATURE:
<223> OTHER INFORMATION: Luciferase gene

<400> SEQUENCE: 7

```
atggaagacg ccaaaaacat aaagaaaggc ccggcgccat tctatccgct ggaagatgga    60
aagatggaac cgctggagag caactgcata aggctatgaa gagatacgcc ctggttcctg    120
gaacaattgc ttttacagat gcacatatcg aggtggacat cacttacgct gagtacttcg    180
aaatgtccgt tcggttggca gaagctatga acgatatggg ctgaataca atcacagaa     240 tcgtcgtatg cagtgaaaac tctcttcaat tctttatgcc ggtgttgggc gcgttattta    300
tcggagttgc agttgcgccc gcgaacgaca tttataatga acgtgaattg ctcaacagta    360
tgggcatttc gcagcctacc gtggtgttcg ttccaaaaa ggggttgcaa aaaatttga     420 acgtgcaaaa aaagctccca atcatccaaa aaattattat catggattct aaaacggatt    480
accagggatt tcagtcgatg tacacgttcg tcacatctca tctacctccc ggttttaatg    540
aatacgattt tgtgccagag tccttcgata gggacaagac aattgcactg atcatgaact    600
cctctggatc tactggtctg cctaaaggtg tcgctctgcc tcatagaact gcctgcgtga    660
gattctcgca tgccagagat cctatttttg gcaatcaaat cattccggat actgcgattt    720
taagtgttgt tccattccat cacggttttg gaatgtttac tacactcgga tatttgatat    780
gtggatttcg agtcgtctta atgtatagat ttgaagaaga ctgtttctg aggagccttc     840 aggattacaa gattcaaagt gcgctgctgg tgccaaccct attctccttc ttcgccaaaa    900
gcactctgat tgacaaatac gatttatcta atttacacga aattgcttct ggtggcgctc    960
ccctctctaa ggaagtcggg gaagcggttg ccaagaggtt ccatctgcca ggtatcaggc    1020
aaggatatgg gctcactgag actacatcag ctattctgat tacacccgag gggatgata    1080
```

```
aaccgggcgc ggtcggtaaa gttgttccat tttttgaagc gaaggttgtg gatctggata    1140
ccgggaaaac gctgggcgtt aatcaaagag gcgaactgtg tgtgagaggt cctatgatta    1200
tgtccggtta tgtaaacaat ccggaagcga ccaacgcctt gattgacaag gatggatggc    1260
tacattctgg agacatagct tactgggacg aagacgaaca cttcttcatc gttgaccgcc    1320
tgaagtctct gattaagtac aaaggctatc aggtggctcc cgctgaattg gaatccatct    1380
tgctccaaca ccccaacatc ttcgacgcag gtgtcgcagg tcttcccgac gatgacgccg    1440
gtgaacttcc cgccgccgtt gttgttttgg agcacggaaa gacgatgacg gaaaaagaga    1500
tcgtggatta cgtcgccagt caagtaacaa ccgcgaaaaa gttgcgcgga ggagttgtgt    1560
ttgtggacga agtaccgaaa ggtcttaccg gaaaactcga cgcaagaaaa atcagagaga    1620
tcctcataaa ggccaagaag ggcggaaaga tcgccgtgta a                        1661

<210> SEQ ID NO 8
<211> LENGTH: 52
<212> TYPE: DNA
<213> ORGANISM: Artificial
<220> FEATURE:
<223> OTHER INFORMATION: c-myc tag

<400> SEQUENCE: 8
agcttatcat ggagcagaaa ctcatctctg aagaagatct ggcccgggcg tc            52

<210> SEQ ID NO 9
<211> LENGTH: 52
<212> TYPE: DNA
<213> ORGANISM: Artificial
<220> FEATURE:
<223> OTHER INFORMATION: c-myc tag

<400> SEQUENCE: 9
gatggacgcc cgggccagat cttcttcaga gatgagtttc tgctccatga ta            52

<210> SEQ ID NO 10
<211> LENGTH: 1706
<212> TYPE: DNA
<213> ORGANISM: Artificial
<220> FEATURE:
<223> OTHER INFORMATION: Fusion gene of c-myc tag and luciferase gene

<400> SEQUENCE: 10
atggagcaga aactcatctc tgaagaagat ctggcccggg cgtccatgga agacgccaaa    60
aacataaaga aaggcccggc gccattctat ccgctggaag atggaaagat ggaaccgctg    120
gagagcaact gcataaggct atgaagagat acgccctggt tcctggaaca attgctttta    180
cagatgcaca tatcgaggtg gacatcactt acgctgagta cttcgaaatg tccgttcggt    240
tggcagaagc tatgaaacga tatgggctga atacaaatca cagaatcgtc gtatgcagtg    300
aaaactctct tcaattcttt atgccggtgt tgggcgcgtt atttatcgga gttgcagttg    360
cgcccgcgaa cgacatttat aatgaacgtg aattgctcaa cagtatgggc atttcgcagc    420
ctaccgtggt gttcgtttcc aaaaaggggt tgcaaaaaat tttgaacgtg caaaaaaagc    480
tcccaatcat ccaaaaaatt attatcatgg attctaaaac ggattaccag ggatttcagt    540
cgatgtacac gttcgtcaca tctcatctac ctcccggttt taatgaatac gattttgtgc    600
cagagtcctt cgatagggac aagacaattg cactgatcat gaactcctct ggatctactg    660
gtctgcctaa aggtgtcgct ctgcctcata gaactgcctg cgtgagattc tcgcatgcca    720
gagatcctat ttttggcaat caaatcattc cggatactgc gattttaagt gttgttccat    780
```

| | |
|---|---|
| tccatcacgg tttttggaatg tttactacac tcggatatttt gatatgtgga tttcgagtcg | 840 |
| tcttaatgta tagatttgaa gaagagctgt ttctgaggag ccttcaggat tacaagattc | 900 |
| aaagtgcgct gctggtgcca accctattct ccttcttcgc caaaagcact ctgattgaca | 960 |
| aatacgattt atctaattta cacgaaattg cttctggtgg cgctcccctc tctaaggaag | 1020 |
| tcggggaagc ggttgccaag aggttccatc tgccaggtat caggcaagga tatgggctca | 1080 |
| ctgagactac atcagctatt ctgattacac ccgaggggga tgataaaccg ggcgcggtcg | 1140 |
| gtaaagttgt tccatttttt gaagcgaagg ttgtggatct ggataccggg aaaacgctgg | 1200 |
| gcgttaatca aagaggcgaa ctgtgtgtga gaggtcctat gattatgtcc ggttatgtaa | 1260 |
| acaatccgga agcgaccaac gccttgattg acaaggatgg atggctacat tctggagaca | 1320 |
| tagcttactg ggacgaagac gaacacttct tcatcgttga ccgcctgaag tctctgatta | 1380 |
| agtacaaagg ctatcaggtg gctcccgctg aattggaatc catcttgctc caacacccca | 1440 |
| acatcttcga cgcaggtgtc gcaggtcttc ccgacgatga cgccggtgaa cttcccgccg | 1500 |
| ccgttgttgt tttggagcac ggaaagacga tgacggaaaa agagatcgtg gattacgtcg | 1560 |
| ccagtcaagt aacaaccgcg aaaaagttgc gcggaggagt tgtgtttgtg gacgaagtac | 1620 |
| cgaaaggtct taccggaaaa ctcgacgcaa gaaaaatcag agagatcctc ataaaggcca | 1680 |
| agaagggcgg aaagatcgcc gtgtaa | 1706 |

```
<210> SEQ ID NO 11
<211> LENGTH: 212
<212> TYPE: DNA
<213> ORGANISM: Artificial
<220> FEATURE:
<223> OTHER INFORMATION: SV40 virus late poly(A) addition signal

<400> SEQUENCE: 11
```

| | |
|---|---|
| aagatacatt gatgagtttg gacaaaccac aactagaatg cagtgaaaaa aatgctttat | 60 |
| ttgtgaaatt tgtgatgcta ttgctttatt tgtaaccatt ataagctgca ataaacaagt | 120 |
| taacaacaac aattgcattc attttatgtt tcaggttcag ggggaggtgt gggaggtttt | 180 |
| ttaaagcaag taaaacctct acaaatgtgg ta | 212 |

```
<210> SEQ ID NO 12
<211> LENGTH: 145
<212> TYPE: DNA
<213> ORGANISM: Artificial
<220> FEATURE:
<223> OTHER INFORMATION: TH gene AhR binding enhancer

<400> SEQUENCE: 12
```

| | |
|---|---|
| gccagcccct gtcttcatgt cgtgtctagg gcggagggtg attcagaggc agtgcctgcg | 60 |
| acagtggatg cagtcttcat gtcgtgtcta gggcggaggg tgattcagag gcaggtgcct | 120 |
| gcgacagtgg atgcaattag atcta | 145 |

```
<210> SEQ ID NO 13
<211> LENGTH: 16
<212> TYPE: DNA
<213> ORGANISM: Artificial
<220> FEATURE:
<223> OTHER INFORMATION: Forward primer for amplifying TH gene AhR
      binding enhancer

<400> SEQUENCE: 13
```

| | |
|---|---|
| gccagcccct gtcttc | 16 |

```
<210> SEQ ID NO 14
<211> LENGTH: 16
<212> TYPE: DNA
<213> ORGANISM: Artificial
<220> FEATURE:
<223> OTHER INFORMATION: Reverse primer for amplifying TH gene AhR
      binding enhancer

<400> SEQUENCE: 14
tagatctaat tgcatc                                                      16

<210> SEQ ID NO 15
<211> LENGTH: 24
<212> TYPE: DNA
<213> ORGANISM: Artificial
<220> FEATURE:
<223> OTHER INFORMATION: Forward primer for amplifying luciferase gene

<400> SEQUENCE: 15
gcgaaggttg tggatctgga tacc                                             24

<210> SEQ ID NO 16
<211> LENGTH: 24
<212> TYPE: DNA
<213> ORGANISM: Artificial
<220> FEATURE:
<223> OTHER INFORMATION: Reverse primer for amplifying luciferase gene

<400> SEQUENCE: 16
cctttcggta cttcgtccac aaac                                             24

<210> SEQ ID NO 17
<211> LENGTH: 2500
<212> TYPE: DNA
<213> ORGANISM: Mus musculus
<220> FEATURE:
<223> OTHER INFORMATION: Transcriptional regulatory region derived from
      mouse tyrosine hydroxylase gene

<400> SEQUENCE: 17
agggcttctc tgtgcccaca gatgctttag atcttggcac agtgtggtct accagctgtc        60
tctctctgtg tatatatatg tatttcatag acagtgtaca gtggcctggt tgtgctatc       120 aggctggata tggacagagg caagagtttg tggcagcagt tatctcccaa gagagtccaa      180
agacatcatg tttttcaagtt taggccaggt gctacttgag agagctcaga cacagacaaa     240
ggtctggaga gcacatgtcc tccaccccca cctagcttct gttgcaagca cctccagccg      300
agacaagaga acgaattaaa aagcaatatt tgtgtcagtg taagacattt gccgaaaggt      360
taaatccaca ttcgtgttgc tgcagagcag cccctatgc aggatttgtt agatacagct       420
ccgtcctacc ctgtgccagc tgagcaaacg ccaggctggg tggggtggaa cccagcctgg      480
gtttgcctca ccctgcaatc cccccagcac cctctaaagg aggaccctgt ggtgggcatg      540
cagacctagg gactgggcat agataaacctt tgggtttggg caacagcccc cactcctcag     600
gattgaaggc taaggtgcag ccagctctgc cttcatggtg ggaatgtctc cacgtgaccc      660
cttttctggc tgtggagaac actcagagaa gagtcctggg atgccaggca ggccagggat      720
gtgctgggca tgttgagaca ggagtgggct aagccagcag agttgctgac ccaggaagag      780
ttcagaaagg ggcatggaac atgggagggg gtccatagtg agagagagca ggcagtgcag      840
agtaaatagt ccctgagctg ggggttatgg gatttgcagg agcttgctca gagaaggcag      900
aggagagatg ctgcgccaag ctgggtatca cagagcctca gactcctgga acaggaactg      960
tgggggtcag gtcagcaggg gaggttaggg agtgttccct ttgtactgac ttagcattta     1020
```

```
                                                  -continued tcctgcttct aggggggaag gggggccagt gggggatgca cagcaaggca gtgatgtggc    1080
aggcagcctg cgggagctcc tggttcctgg tgtgaaaaag ctgggaagga agagggctgg    1140
gtctggtaag tacagcaggc agttggctcc tgagagtcca agccctgtct agagggtgga    1200
gtgagatttc agagggagag ctaaacgggg tgggggctgg ggagtccagg cttctggctc    1260
ctgctaatac tcagtgtgct gggtcctcag aacctcaggg tggccatttt cagggtgaga    1320
gctctgtcct ttggcacttc tgcagactcc agtatccaga ggaataaaga tggtactctt    1380
cctcagttcc cttagtgaga ggacaccttt ctctgaaggg cttgggcagt tgtcctgaac    1440
cattgcctga aggaaggact tgactccagg gacatagaat gggctcagca taagtcccct    1500
gtagtagaga aaggtcccct ctctggtctc cttagagatc ctgtttcctt ggctgaggaa    1560
gctagggtgg atctttgtgt aagtgggtgt ggatgctcac tggaaatcaa aaggcccctt    1620
ggtgttagac cttggggtgc catgggagag ttgatcactg agtgcgccct tacatggggg    1680
ccagctgaga atgggctgc ctctagctcg agaccatgat gcaggagtg agtggggag     1740 ttcaggatac tcttaactaa agcagaggtc tgtcccccca gggaggggag gtcagaagac    1800
cctagggaga tgccaaaggc tagggttggc accatgttgc aggctgtgtc ttcaaggaga    1860
tgataatcag aggaatcgaa cctgcaaaag tgggccagtc ttagatacac tatagaggaa    1920
taatcttctg aaacattctg tgtctcatag gacctgcctg aggacccagc cccagtgcca    1980
gcacatacac tggggcagtg agtagatagt atactttgtt acatgggctg gggggacatg    2040
gcctgtgccc tggaggggac ttgaagacat ccaaaaagct agtgagaggg ctcctagatt    2100
tatttgtctc caagggctat atatagcctt cctaacatga acccttgggt aatccagcat    2160
gggcgctccc atatgccctg gtttgattag agagctctag atgtctcctg tcccagaaca    2220
ccagccagcc cctgtcttca tgtcgtgtct agggcggagg gtgattcaga ggcaggtgcc    2280
tgcgacagtg gatgcaatta gatctaatgg gacggaggcc tctctcgtcc gtcgccctcg    2340
ctctgtgccc accccgcct ccctcaggca cagcaggcgt ggagaggatg cgcaggaggt     2400
aggaggtggg ggacccagag gggctttgac gtcagcctgg cctttaagag gccgcctgcc    2460
tggcaagggc tgtggagaca gaactcggga ccaccagctt                         2500
```

GENETICALLY MODIFIED ANIMAL FOR USE IN EVALUATING HARMFULNESS OF TEST SUBSTANCE

CROSS-REFERENCE TO RELATED APPLICATIONS

This application is based upon and claims the benefit of priority from prior Japanese Patent Application No. 2008-244392, filed Sep. 24, 2008, the entire contents of which are incorporated herein by reference.

BACKGROUND OF THE INVENTION

1. Field of the Invention

The present invention relates to a genetically modified animal for use in evaluating the harmfulness of test substances and a method for evaluating the action of test substances in the genetically modified animal or part thereof.

2. Description of the Related Art

There have been concerns about the effect of environmental pollutant chemicals such as dioxins, PCBs, brominated flame retardants, and some agricultural chemicals on human health. In addition, many of various chemicals used in industrial activity or everyday life may have an unknown effect on human health.

Such chemicals are considered to act on biological functions such as liver function, reproductive function, immune function, and neural function and to have a harmful effect on human health.

Therefore, techniques for detecting and/or evaluating a biological function on which a specific chemical substance can act are very important for definition of handling or control of chemicals or for treatment of a human exposed to chemicals. Particularly, in recent years, it has been pointed out that exposure to some chemicals during the fetal or infant period could cause infants to have autism or higher brain dysfunction such as hyperactivity disorder. Therefore, there has been a demand for the development of techniques to evaluate the effect of chemicals on the neural function.

Currently, techniques to evaluate the effect of chemicals on biological functions are broadly classified into in vitro evaluation techniques using single cells and in vivo evaluation techniques using animal individuals.

The in vitro evaluation techniques include a technique of using mouse liver-derived Hepalc1c7 cells to evaluate the effect of test substances on the liver function (U.S. Pat. No. 5,854,010) and a method of using human mammary gland-derived MCF-7 cells to evaluate the effect of test substances on the reproductive function (JP-A 2002-253231). As regards the neural function, an in vitro evaluation method using mouse Neuro2a neuroblastoma cells has already been reported by the present applicant. This method includes transfecting the cells with a reporter gene under the control of a promoter having an aryl hydrocarbon receptor-binding enhancer sequence for a tyrosine hydroxylase gene (TH) gene and a TH gene core promoter sequence to produce genetically modified cells and evaluating the effect of a test substance on the central nervous system in the genetically modified cells. Concerning the in vivo evaluation techniques, there have been reported methods for evaluating the effect of test substances on the reproductive function, which use genetically modified mice produced by the introduction of a reporter gene under the control of an Mvh gene or c-mos gene promoter (JP-A 2001-8577 and 2001-8578).

BRIEF SUMMARY OF THE INVENTION

In view of the above circumstances, an object of the invention is to provide a genetically modified animal for use in evaluating the harmfulness or effect of test substances on a living body and a method for evaluating the effect of test substances in the animal or part thereof. A specific object of the invention is to provide a genetically modified animal for use in evaluating the effect of test substances on the neural function and a method of using the genetically modified animal or part thereof to evaluate the effect of test substances on the neural function.

To achieve the object, the invention provides:

(1) a genetically modified animal including introduced DNA in which an aryl hydrocarbon receptor-binding enhancer located 5'-upstream of a tyrosine hydroxylase gene, a promoter of any type, a reporter gene, and a poly(A) addition signal are functionally linked; and (2) a method for determining the harmfulness of a test substance, including bringing the test substance into contact with the genetically modified animal of item (1) or part thereof and detecting the expression of the reporter gene.

The invention provides a genetically modified animal for use in evaluating the harmfulness or effect of a test substance on a living body and a method of evaluating the effect of a test substance in the animal or part thereof. Specifically, the invention provides a genetically modified animal for use in evaluating the effect of a test substance on a neural function and a method of using the genetically modified animal or part thereof to evaluate the effect of a test substance on a neural function.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is a graph showing a TCDD concentration-dependent increase in the degree of luminescence.

DETAILED DESCRIPTION OF THE INVENTION

Figure 1:
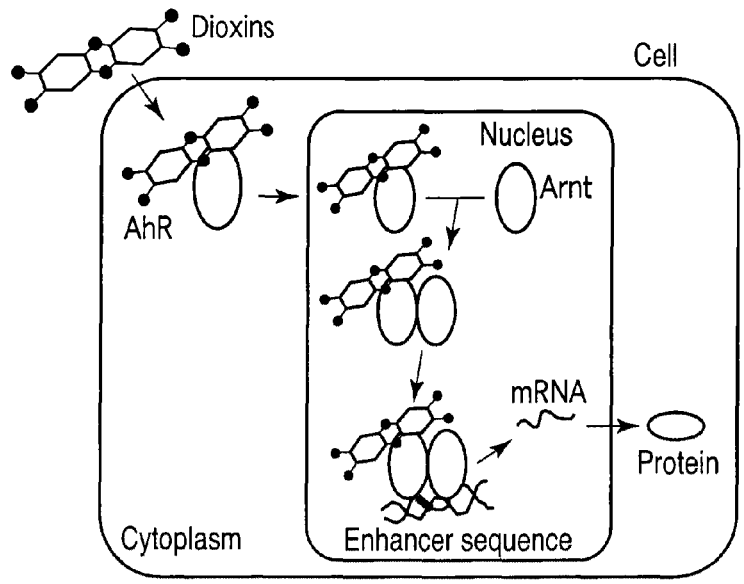
FIG. 1 is a diagram showing a gene transcription activating mechanism.

At present, there has been reported an in vitro evaluation technique of using mouse Neuro2a neuroblastoma cells to evaluate the effect of test substances on the neural function. In such an evaluation technique using single cells, however, it is difficult to precisely evaluate the effect of test substances at the individual animal level. For example, this is considered to be because there is a high possibility that single cells will not necessarily reproduce the uptake or distribution of test substances or the metabolism of test substances in the same manner as in an animal individual. Therefore, it is considered that when the effect of test substances on biological functions is evaluated, an in vitro evaluation technique should preferably be used in combination with an in vivo evaluation technique. Thus, the inventors have noted that conventionally, in vivo evaluation techniques effective for evaluating neural functions have not yet been established, and have worked on the development of in vivo evaluation techniques to evaluate the effect of test substances on neural functions.

The TH gene is a gene encoding a tyrosine hydroxylase which is a rate-limiting enzyme of dopamine biosynthesis, and it is known that the modification of the expression of the gene by exposure to chemicals can affect neural functions. The inventors have made investigations on in vivo techniques of using the expression of the TH gene as an indicator to evaluate the effect of chemicals on neural functions. As a result, the inventors have made a genetically modified mouse having an introduced DNA in which an aryl hydrocarbon receptor (hereinafter also referred to as "AhR")-binding enhancer of the TH gene, any promoter, a reporter gene, and a poly(A) addition signal are linked together.

The genetically modified mouse of the invention expresses the reporter gene in the central nervous system, and the expression correlates with the expression of the TH gene. Therefore, the use of the genetically modified mouse allows easy and fast evaluation of the effect of test substances on the expression of the TH gene, namely, the effect of test substances on the central nervous system, by in vivo biochemical measurement using the expression of the reporter gene as an indicator.

[Genetically Modified Mouse]

The invention will be described in detail below. The genetically modified mouse of the invention may be obtained by transfecting a fertilized egg or an early embryo with DNA in which an AhR-binding enhancer for a TH gene, a promoter of any type, a reporter gene, and a poly(A) addition signal are functionally linked.

As used herein, the term "functionally linked" means that the regions are linked in such a way that each region can perform its function. For example, a functionally linked promoter or reporter gene is a promoter or reporter gene linked in such a way that the promoter can be active or the reporter gene expression can be enhanced in the genetically modified animal according to the invention.

In an embodiment of the invention, the DNA to be introduced into a mouse has an AhR-binding enhancer, any promoter, and a reporter gene.

[Enhancer]

As used herein, the term "enhancer" refers to a specific nucleotide sequence that exists on a genome, can bind a transcription factor activated by a substrate, and has the function of activating the transcription of a downstream gene upon binding of the transcription factor. The AhR-binding enhancer is a nucleotide sequence that can bind AhR (a receptor-type transcription factor) activated by binding of dioxin and has the function of activating the transcription of the downstream gene upon the binding of AhR.

In an embodiment of the invention, the AhR-binding enhancer should include the nucleotide sequence represented by SEQ ID NO:1 as the minimal sequence. Those of skill in the art may select other AhR-binding enhancers from those known in the art or from those that comprise SEQ ID NO: 1, which are at least 80%, 90%, 95%, or 96.8% identical to SEQ ID NO: 1, or which differ from SEQ ID NO: 1 by the deletion, substitution or addition of 1, 2, 3, 4, 5 bases.

```
                                        [SEQ ID NO: 1]
TH gene AHR-binding enhancer (1)
[Minimal sequence]
GTCTTCATGT CGTGTCTAGG GCGG      (SEQ ID NO: 1)
```

This nucleotide sequence is derived from a region (−214 by to −237 bp) 5'-upstream of a mouse TH gene. In an embodiment of the invention, a nucleotide sequence in a wider region 5'-upstream of the TH gene, such as the nucleotide sequence represented by SEQ ID NO:2 (−175 by to −237 bp), may be used as the AhR-binding enhancer, as long as it includes the nucleotide sequence represented by SEQ ID NO:1.

```
                                        [SEQ ID NO: 2]
TH gene AHR-binding enhancer (2)
[63 bp sequence]
                                        (SEQ ID NO: 2)
GTCTTCATGT CGTGTCTAGG GCGGAGGGTG ATTCAGAGGC

AGGTGCCTGC GACAGTGGAT GCA (Underline: SEQ ID NO: 1 = AHR-binding enhancer
(1))
```

Two or more AhR-binding enhancers may also be linked and used together, and the AhR-binding enhancer may be used in an orientation the same as the orientation on the mouse genome (forward) or in an orientation different from the orientation on the mouse genome (reverse). When two or more AhR-binding enhancers are linked and used together, a linking moiety including a linker sequence of about 1 to about 50 bases may be interposed between the enhancers, as long as the function of the enhancer is conserved. In an embodiment of the invention, another example of the AhR-binding enhancer may be the nucleotide sequence represented by SEQ ID NO:3.

```
                                        [SEQ ID NO: 3]
TH gene AHR-binding enhancer (3)
[SEQ ID NO: 2 x6, in the orientational order of
reverse, reverse, forward, forward, forward, and
forward]
                                        (SEQ ID NO: 3)
TAGATCTAAT TGCATCCACT TCGCAGGCAC CTCCTCTGAA

TCACCCTCCG CCCTAGACAC GACATGAAGA CTGCATCCAC

TGTCGCAGGC ACCTGCCTCT GAATCACCCT CCGCCCTAGA

CACGACATGA AGACAGGGGC TGGCGCCAGC CCCTGTCTTC

ATGTCGTGTC TAGGGCGGAG GGTGATTCAG AGGCAGGTGC

CTGCGACAGT GGATGCAGTC TTCATGTCGT GTCTAGGGCG

GAGGGTGATT CAGAGGAGGT GCCTGCGACA GTGGATGCAA

TTAGATCTAG CCAGCCCCTG TCTTCATGTC GTGTCTAGGG

CGGAGGGTGA TTCAGAGGCA GGTGCCTGCG ACAGTGGATG

CAGTCTTCAT GTCGTGTCTA GGGCGGAGGG TGATTCAGAG

GCAGGTGCCT GCGACAGTGG ATGCAATTAG ATCTA (Underline: SEQ ID NO: 2 = AHR-binding enhancer
(2) x1)
```

This enhancer includes six SEQ ID NO: 2 nucleotide sequences linked together in the orientational order of reverse, reverse, forward, forward, forward, and forward from the 5' side. This enhancer may be prepared by a combination of known genetic manipulation methods including polymerase chain reaction (PCR) and so on.

The enhancer may include one or more SEQ ID NO: 1 or NO: 2 nucleotide sequences, typically one, two, three, four, five, six, seven, eight, nine, ten, or more SEQ ID NO: 1 or NO: 2 nucleotide sequences, preferably two to eight SEQ ID NO: 1 or NO: 2 nucleotide sequences, most preferably three to six SEQ ID NO: 1 or NO: 2 nucleotide sequences. As described above, the orientation of the SEQ ID NO: 1 or NO: 2 sequence in the enhancer may be the same as the orientation of the enhancer sequence 5'-upstream of the mouse TH gene with respect to the TH structural gene (namely, the forward orientation), different from that (namely, the reverse orientation), or a combination thereof.

In an embodiment of the invention, the enhancer region to be used may be any other region than SEQ ID NOs: 1, 2 and 3, as long as it can enhance the activity of the transcription of the downstream gene in response to the test substance in the transcriptional regulatory region of the TH gene. For example, the transcriptional regulatory region of the TH gene is the region (2.5 kb) shown in SEQ ID NO: 17. The transcriptional regulatory region of the TH gene may be a region (2,500 bp) 5'-upstream of the TH gene in any animal species, such as a region (2,500 bp) 5'-upstream of the human, mouse, or rat TH gene.

The enhancer region capable of enhancing the activity of the transcription of the downstream gene in response to the test substance may also contain a region capable of enhancing the promoter activity.

[Promoter]

The promoter is a nucleotide sequence that includes an RNA polymerase-binding sequence and is essential to initiate the transcription of a gene. In an embodiment of the invention, the promoter is preferably the TH gene promoter shown in SEQ ID NO:4.

```
                                      [SEQ ID NO: 4]
TH gene promoter
                                      (SEQ ID NO: 4)
GTGGGGACC CAGAGGGGCT TTGACGTCAG CCTGGCCTTT

AAGAGGCCGC CTGCCTGGCA AGGGCTGTGG AGACAGAACT

CGGGACCACC AGCTT
```

The promoter to be used is not limited thereto and may be any other known promoter capable of being active in a mammal, such as a simian virus 40 (SV40) early or late promoter, a human herpes virus 1 thymidine kinase promoter, or a cytomegalovirus promoter.

The promoter may be obtained by a combination of known genetic manipulation methods including polymerase chain reaction (PCR) and so on. The resulting promoter may be ligated to the 3'-end of the enhancer with a DNA ligase and so on. When the enhancer and the promoter are linked to each other, a linking moiety including a linker sequence of about 1 to 50 bases may be interposed therebetween, as long as the function of each of the enhancer and the promoter is conserved.

In an embodiment of the invention, an example of the nucleotide sequence including the enhancer and the promoter that are functionally linked together includes the nucleotide sequence shown in SEQ ID NO: 5.

```
                                      [SEQ ID NO: 5]
AhR-binding enhancer (3) + TH gene promoter
[SEQ ID NO: 3 + SEQ ID NO: 4]
                                      (SEQ ID NO: 5)
TAGATCTAAT TGCATCCACT TCGCAGGCAC CTCCTCTGAA

TCACCCTCCG CCCTAGACAC GACATGAAGA CTGCATCCAC

TGTCGCAGGC ACCTGCCTCT GAATCACCCT CCGCCCTAGA

CACGACATGA AGACAGGGGC TGGCGCCAGC CCCTGTCTTC

ATGTCGTGTC TAGGGCGGAG GGTGATTCAG AGGCAGGTGC

CTGCGACAGT GGATGCAGTC TTCATGTCGT GTCTAGGGCG

GAGGGTGATT CAGAGGAGGT GCCTGCGACA GTGGATGCAA

TTAGATCTAG CCAGCCCCTG TCTTCATGTC GTGTCTAGGG

CGGAGGGTGA TTCAGAGGCA GGTGCCTGCG ACAGTGGATG

CAGTCTTCAT GTCGTGTCTA GGGCGGAGGG TGATTCAGAG

GCAGGTGCCT GCGACAGTGG ATGCAATTAG ATCTAGGGCT

CGAGGTGGGG GACCCAGAGG GGCTTTGACG TCAGCCTGGC

CTTTAAGAGG CCGCCTGCCT GGCAAGGGCT GTGGAGACAG

AACTCGGGAC CACCAGCTT
```

(Underline: SEQ ID NO: 4 = TH gene promoter)

The nucleotide sequence represented by SEQ ID NO: 5 includes the enhancer shown in SEQ ID NO: 3 and the TH gene promoter shown in SEQ ID NO: 4 that are linked with a linker sequence interposed therebetween.

[Reporter Gene]

In an embodiment of the invention, the reporter gene is preferably a luciferase gene encoding an enzyme which catalyzes bioluminescence reaction in firefly, in view of enzyme reaction rate and reaction quantification. However, the reporter gene to be used is not limited thereto and may be any other known reporter gene such as a green fluorescent protein gene, a β-galactosidase gene, or a chloramphenicol acetyltransferase gene.

The reporter gene to be used may have the original nucleotide sequence of a naturally-occurring gene or may be a gene modified by mutagenesis methods such as site-directed mutagenesis. Alternatively, the reporter gene to be used may have a modified nucleotide sequence to express a fusion protein with another protein or polypeptide, as long as the function of the protein encoded by the reporter gene is not lost.

A commercially available gene may be purchased and used as the reporter gene, or the reporter gene may be prepared by a combination of known genetic manipulation methods including polymerase chain reaction (PCR) and so on. In the case of the luciferase gene, for example, the firefly luciferase gene shown in SEQ ID NO:7 may be used, which is incorporated in PGV vector series (Toyo B-Net Co., Ltd.).

```
                                      [SEQ ID NO: 7]
Luciferase gene
                                      (SEQ ID NO: 7)
ATGGAAGACG CCAAAAACAT AAAGAAAGG CCCGGCGCCA

TTCTATCCGC TGGAAGATGG AAAGATGGAA CCGCTGGAG

AGCAACTGCA TAAGGCTATG AAGAGATACG CCCTGGTTCC

TGGAACAAT TGCTTTTACA GATGCACATA TCGAGGTGGA
```

-continued
```
CATCACTTAC GCTGAGTAC TTCGAAATGT CCGTTCGGTT

GGCAGAAGCT ATGAAACGAT ATGGGCTGA ATACAAATCA

CAGAATCGTC GTATGCAGTG AAAACTCTCT TCAATTCTT

TATGCCGGTG TTGGGCGCGT TATTTATCGG AGTTGCAGTT

GCGCCCGCGA ACGACATTTA TAATGAACGT GAATTGCTCA

ACAGTATGGG CATTTCGCAG CCTACCGTGG TGTTCGTTTC

CAAAAGGGG TTGCAAAAAA TTTTGAACGT GCAAAAAAG

CTCCCAATCA TCCAAAAAAT TATTATCATG GATTCTAAAA

CGGATTACCA GGGATTTCAG TCGATGTACA CGTTCGTCAC

ATCTCATCTA CCTCCCGGTT TAATGAATA CGATTTTGTG

CCAGAGTCCT TCGATAGGGA CAAGACAATT GCACTGATCA

TGAACTCCTC TGGATCTACT GGTCTGCCTA AAGGTGTCGC

TCTGCCTCAT AGAACTGCCT GCGTGAGATT CTCGCATGCC

AGAGATCCTA TTTTTGGCAA TCAAATCATT CCGGATACTG

CGATTTTAAG TGTTGTTCCA TTCCATCACG GTTTTGGAAT

GTTTACTACA CTCGGATATT TGATATGTGG ATTTCGAGTC

GTCTTAATGT ATAGATTTGA AGAAGAGCTG TTTCTGAGGA

GCCTTCAGGA TTACAAGATT CAAAGTGCGC TGCTGGTGCC

AACCCTATTC TCCTTCTTCG CCAAAAGCAC TCTGATTGAC

AAATACGATT TATCTAATTT ACACGAAATT GCTTCTGGTG

GCGCTCCCCT CTCTAAGGAA GTCGGGGAAG CGGTTGCCAA

GAGGTTCCAT CTGCCAGGTA TCAGGCAAGG ATATGGGCTC

ACTGAGACTA CATCAGCTAT TCTGATTACA CCCGAGGGGG

ATGATAAACC GGGCGCGGTC GGTAAAGTTG TTCCATTTTT

TGAAGCGAAG GTTGTGGATC TGGATACCGG GAAAACGCTG

GGCGTTAATC AAAGAGGCGA ACTGTGTGTG AGAGGTCCTA

TGATTATGTC CGGTTATGTA AACAATCCGG AAGCGACCAA

CGCCTTGATT GACAAGGATG GATGGCTACA TTCTGGAGAC

ATAGCTTACT GGGACGAAGA CGAACACTTC TTCATCGTTG

ACCGCCTGAA GTCTCTGATT AAGTACAAAG GCTATCAGGT

GGCTCCCGCT GAATTGGAAT CCATCTTGCT CCAACACCCC

AACATCTTCG ACGCAGGTGT CGCAGGTCTT CCCGACGATG

ACGCCGGTGA ACTTCCCGCC GCCGTTGTTG TTTTGGAGCA

CGGAAAGACG ATGACGGAAA AAGAGATCGT GGATTACGTC

GCCAGTCAAG TAACAACCGC GAAAAGTTG CGCGGAGGAG

TTGTGTTTGT GGACGAAGTA CCGAAAGGTC TTACCGGAAA

ACTCGACGCA AGAAAAATCA GAGAGATCCT CATAAAGGCC

AAGAAGGGCG GAAAGATCGC CGTGTAA
```

When the luciferase gene of this vector is used for a fusion gene, DNA encoding a protein or peptide to be fused may be inserted in frame into the NcoI site incorporated on the initiation codon of the luciferase gene. In order to prepare a fusion gene encoding a luciferase protein fused with a c-myc tag sequence at the N-terminus, for example, the nucleotide sequences represented by SEQ ID NO: 8 and SEQ ID NO: 9 may be annealed to each other and then inserted between the Hind III and Nco I sites of the vector PGV-P2, so that the c-myc-tagged luciferase fusion gene shown in SEQ ID NO: 10 can be prepared.

```
                                          [SEQ ID NO: 8]
c-myc tag (forward)
                                          (SEQ ID NO: 8)
AGCTTATCAT GGAGCAGAAA CTCATCTCTG AAGAAGATCT

GGCCCGGGCG TC (Underline: c-myc tag coding sequence)

[SEQ ID NO: 9]
c-myc tag (reverse)
                                          (SEQ ID NO: 9)
GATGGACGCC CGGGCCAGAT CTTCTTCAGA GATGAGTTTC

TGCTCCATGA TA

[SEQ ID NO: 10]
c-myc tag-luciferase fusion gene
                                          (SEQ ID NO: 10)
ATGGAGCAGA AACTCATCTC TGAAGAAGAT CTGGCCCGGG

CGTCCATGGA AGACGCCAAA AACATAAAGA AAGGCCCGGC

GCCATTCTAT CCGCTGGAAG ATGGAAAGAT GGAACCGCTG

GAGAGCAACT GCATAAGGCT ATGAAGAGAT ACGCCCTGGT

TCCTGGAACA ATTGCTTTTA CAGATGCACA TATCGAGGTG

GACATCACTT ACGCTGAGTA CTTCGAAATG TCCGTTCGGT

TGGCAGAAGC TATGAAACGA TATGGGCTGA ATACAAATCA

CAGAATCGTC GTATGCAGTG AAAACTCTCT TCAATTCTTT

ATGCCGGTGT TGGGCGCGTT ATTTATCGGA GTTGCAGTTG

CGCCCGCGAA CGACATTTAT AATGAACGTG AATTGCTCAA

CAGTATGGGC ATTTCGCAGC CTACCGTGGT GTTCGTTTCC

AAAAAGGGGT TGCAAAAAAT TTTGAACGTG CAAAAAAAGC

TCCCAATCAT CCAAAAAATT ATTATCATGG ATTCTAAAAC

GGATTACCAG GGATTTCAGT CGATGTACAC GTTCGTCACA

TCTCATCTAC CTCCCGGTTT AATGAATAC GATTTTGTGC

CAGAGTCCTT CGATAGGGAC AAGACAATTG CACTGATCAT

GAACTCCTCT GGATCTACTG GTCTGCCTAA AGGTGTCGCT

CTGCCTCATA GAACTGCCTG CGTGAGATTC TCGCATGCCA

GAGATCCTAT TTTTGGCAAT CAAATCATTC CGGATACTGC

GATTTTAAGT GTTGTTCCAT TCCATCACGG TTTTGGAATG

TTTACTACAC TCGGATATTT GATATGTGGA TTTCGAGTCG

TCTTAATGTA TAGATTTGAA GAAGAGCTGT TTCTGAGGAG

CCTTCAGGAT TACAAGATTC AAAGTGCGCT GCTGGTGCCA

ACCCTATTCT CCTTCTTCGC CAAAAGCACT CTGATTGACA

AATACGATTT ATCTAATTTA CACGAAATTG CTTCTGGTGG

CGCTCCCCTC TCTAAGGAAG TCGGGGAAGC GGTTGCCAAG

AGGTTCCATC TGCCAGGTAT CAGGCAAGGA TATGGGCTCA
```

-continued

```
CTGAGACTAC ATCAGCTATT CTGATTACAC CCGAGGGGGA

TGATAAACCG GGCGCGGTCG GTAAAGTTGT TCCATTTTTT

GAAGCGAAGG TTGTGGATCT GGATACCGGG AAAACGCTGG

GCGTTAATCA AAGAGGCGAA CTGTGTGTGA GAGGTCCTAT

GATTATGTCC GGTTATGTAA ACAATCCGGA AGCGACCAAC

GCCTTGATTG ACAAGGATGG ATGGCTACAT TCTGGAGACA

TAGCTTACTG GGACGAAGAC GAACACTTCT TCATCGTTGA

CCGCCTGAAG TCTCTGATTA AGTACAAAGG CTATCAGGTG

GCTCCCGCTG AATTGGAATC CATCTTGCTC CAACACCCCA

ACATCTTCGA CGCAGGTGTC GCAGGTCTTC CCGACGATGA

CGCCGGTGAA CTTCCCGCCG CCGTTGTTGT TTTGGAGCAC

GGAAAGACGA TGACGGAAAA AGAGATCGTG GATTACGTCG

CCAGTCAAGT AACAACCGCG AAAAAGTTGC GCGGAGGAGT

TGTGTTTGTG GACGAAGTAC CGAAAGGTCT TACCGGAAAA

CTCGACGCAA GAAAAATCAG AGAGATCCTC ATAAAGGCCA

AGAAGGGCGG AAAGATCGCC GTGTAA
```

(Underline: part of SEQ ID NO: 8 = c-myc tag coding sequence)

The reporter protein produced from such a fusion gene can be detected with a tag-specific antibody and therefore is effective for detecting a certain reporter protein to which no effective antibody is available. The reporter gene prepared as described above may be ligated to the nucleotide sequence including the functionally linked enhancer and promoter, for example, the 3'-end of the nucleotide sequence represented by SEQ ID NO: 5, using a DNA ligase and so on. When the promoter and the reporter are linked to each other, a linking moiety including a linker sequence of about 1 to 50 bases may be interposed therebetween, as long as the function of each of the promoter and reporter genes is conserved.

[Poly(A) Addition Signal]

In an embodiment of the invention, the poly(A) addition signal to be used may be any known transcription termination signal sequence capable of functioning to terminate the transcription of a mammal gene. Examples include an SV40 virus late poly(A) addition signal and a bovine growth hormone gene poly(A) addition signal. An example of the SV40 virus late poly(A) addition signal nucleotide sequence is shown in SEQ ID NO: 11.

```
                                        [SEQ ID NO: 11]
    SV40 virus late poly (A) addition signal
                                        (SEQ ID NO: 11)
    AAGATACATT GATGAGTTTG GACAAACCAC AACTAGAATG

CAGTGAAAAA AATGCTTTAT TTGTGAAATT TGTGATGCTA

TTGCTTTATT TGTAACCATT ATAAGCTGCA ATAAACAAGT

TAACAACAAC AATTGCATTC ATTTTATGTT TCAGGTTCAG

GGGGAGGTGT GGGAGGTTTT TTAAAGCAAG TAAAACCTCT

ACAAATGTGG TA
```

However, the SV40 virus late poly(A) addition signal that may be used to carry out the invention is not limited thereto, and modifications of the sequence may also be used, as long as they do not lose the function of serving as a poly(A) addition signal.

The poly(A) addition signal to be used may be linked to the 3'-end of the reporter gene. The reporter gene and the poly(A) addition signal may be ligated using a DNA ligase or the like, or a commercially available vector including the reporter gene and the poly(A) addition signal that are already linked together may be used without modification. A linking moiety including a linker sequence of about 1 to 50 bases may be interposed between the reporter gene and the poly(A) addition signal, as long as the function of each of the reporter gene and the poly(A) addition signal is conserved.

[Introduced DNA]

In an aspect of the invention, DNA including the functionally linked enhancer, promoter, reporter gene, and poly(A) addition signal is introduced into a mouse so that a genetically modified mouse is produced. An example of the DNA to be introduced into a mouse is shown in SEQ ID NO: 6.

```
                                                     [SEQ ID NO: 6]
AhR-binding enhancer (3) + TH gene promoter +
c-myc tag-luciferase gene + SV40 virus late poly
(A) signal [SEQ ID NO: 3 + SEQ ID NO: 4 + SEQ ID
NO: 10 + SEQ ID NO: 11]
                                                     (SEQ ID NO: 6)
TAGATCTAAT TGCATCCACT TCGCAGGCAC CTCCTCTGAA TCACCCTCCG

CCCTAGACAC GACATGAAGA CTGCATCCAC TGTCGCAGGC ACCTGCCTCT

GAATCACCCT CCGCCCTAGA CACGACATGA AGACAGGGGC TGGCGCCAGC

CCCTGTCTTC ATGTCGTGTC TAGGGCGGAG GGTGATTCAG AGGCAGGTGC

CTGCGACAGT GGATGCAGTC TTCATGTCGT GTCTAGGGCG GAGGGTGATT

CAGAGGAGGT GCCTGCGACA GTGGATGCAA TTAGATCTAG CCAGCCCCTG

TCTTCATGTC GTGTCTAGGG CGGAGGGTGA TTCAGAGGCA GGTGCCTGCG

ACAGTGGATG CAGTCTTCAT GTCGTGTCTA GGGCGGAGGG TGATTCAGAG

GCAGGTGCCT GCGACAGTGG ATGCAATTAG ATCTAGGGCT CGAGGTGGGC    (A)

GACCCAGACG GCTTTGACG TCAGCCTGGC CTTTAAGAGG CCGCCTGCCT

GGCAAGGGCT GTGGAGACAG AACTCGGGAC CACCAGCTTA AGCTTATCAT    (B)
```

-continued

```
GGAGCAGAAA CTCATCTCTG AAGAAGATCT GGCCCGGGCG TCCATGGAAG

ACGCCAAAAA CATAAAGAAA GGCCCGGCGC CATTCTATCC GCTGGAAGAT

GGAAAGATGG AACCGCTGGA GAGCAACTGC ATAAGGCTAT GAAGAGATAC

GCCCTGGTTC CTGGAACAAT TGCTTTTACA GATGCACATA TCGAGGTGGA

CATCACTTAC GCTGAGTACT TCGAAATGTC CGTTCGGTTG GCAGAAGCTA

TGAAACGATA TGGGCTGAAT ACAAATCACA GAATCGTCGT ATGCAGTGAA

AACTCTCTTC AATTCTTTAT GCCGGTGTTG GGCGCGTTAT TTATCGGAGT

TGCAGTTGCG CCCGCGAACG ACATTTATAA TGAACGTGAA TTGCTCAACA

GTATCGGCAT TTCGCAGCCT ACCGTGGTGT TCGTTTCCAA AAAGGGGTTG

CAAAAAATTT TGAACGTGCA AAAAAAGCTC CCAATCATCC AAAAAATTAT

TATCATGGAT TCTAAAACGG ATTACCAGGG ATTTCAGTCG ATGTACACGT

TCGTCACATC TCATCTACCT CCCGGTTTTA ATGAATACGA TTTTGTGCCA

GAGTCCTTCG ATAGGGACAA GACAATTGCA CTGATCATGA ACTCCTCTGG

ATCTACTCGT CTGCCTAAAG GTGTCGCTCT GCCTCATAGA ACTGCCTGCG

TGAGATTCTC GCATGCCAGA GATCCTATTT TTGGCAATCA AATCATTCCG

GATACTGCGA TTTTAAGTGT TGTTCCATTC CATCACGGTT TTGGAATGTT

TACTACACTC GGATATTTGA TATGTGGATT TCGAGTCGTC TTAATGTATA

GATTTGAAGA AGAGCTGTTT CTGAGGAGCC TTCAGGATTA CAAGATTCAA

AGTGCGCTGC TGGTGCCAAC CCTATTCTCC TTCTTCGCCA AAAGCACTCT

GATTGACAAA TACGATTTAT CTAATTTACA CGAAATTGCT TCTGGTGGCG

CTCCCCTCTC TAAGGAAGTC GGGGAAGCGG TTGCCAAGAG GTTCCATCTG

CCAGGTATCA GGCAAGGATA TGGGCTCACT GAGACTACAT CAGCTATTCT

GATTACACCC GAGGGGGATG ATAAACCGGG CGCGGTCGGT AAAGTTGTTC

CATTTTTTGA AGCGAAGGTT GTGGATCTGG ATACCGGGAA AACGCTGGGC

GTTAATCAAA GAGGCGAACT GTGTGTGAGA GGTCCTATGA TTATGTCCGG

TTATGTAAAC AATCCGGAAG CGACCAACGC CTTGATTGAC AAGGATGGAT

GGCTACATTC TGGAGACATA GCTTACTGGG ACGAAGACGA ACACTTCTTC

ATCGTTGACC GCCTGAAGTC TCTGATTAAG TACAAAGGCT ATCAGGTGGC

TCCCGCTGAA TTGGAATCCA TCTTGCTCCA ACACCCCAAC ATCTTCGACG

CAGGTGTCGC AGGTCTTCCC GACGATGACG CCGGTGAACT TCCCGCCGCC

GTTGTTGTTT TGGAGCACGG AAAGACGATG ACGGAAAAAG AGATCGTGGA

TTACGTCGCC AGTCAAGTAA CAACCGCGAA AAAGTTGCGC GGAGGAGTTG

TGTTTGTGGA CGAAGTACCG AAAGGTCTTA CCGGAAAACT CGACGCAAGA

AAAATCAGAG AGATCCTCAT AAAGGCCAAG AAGGGCGGAA AGATCGCCGT

GTAATTCTAG AGTCGGGGCG GCCGGCCGCT TCGAGCAGAC ATGATAAGAT  (C)

ACATTGATGA GTTTGGACAA ACCACAACTA GAATGCAGTG AAAAAAATGC

TTTATTTGTG AAATTTGTGA TGCTATTGCT TTATTTGTAA CCATTATAAG

CTGCAATAAA CAAGTTAACA ACAACAATTG CATTCATTTT ATGTTTCAGG
```

```
-continued
TTCAGGGGGA GGTGTGGGAG GTTTTTTAAA GCAAGTAAAA CCTCTACAAA

TGTGGTA
```

(Underline (A): SEQ ID NO: 4 = TH gene promoter)
(Underline (B): SEQ ID NO: 10 = c-myc tag-luciferase fusion gene)
(Underline (C): SEQ ID NO: 11 = SV40 virus late poly (A) addition signal)

The DNA represented by SEQ ID NO:6 includes, in a functionally linked relationship, the nucleotide sequence represented by SEQ ID NO:5 including the enhancer and the promoter linked together; the c-myc-tagged (N-terminus) luciferase gene represented by SEQ ID NO: 10; and the SV40 virus late poly(A) addition signal represented by SEQ ID NO: 11. The DNA also includes a linking moiety having a linker sequence between SEQ ID NO: 5 and SEQ ID NO: 10 and another linking moiety having another linker sequence between SEQ ID NO: 10 and SEQ ID NO: 11.

[Genetically Modified Animal]

The genetically modified mouse may be obtained by a process that includes introducing the DNA into a mouse and selecting a mouse having the DNA in its genome. In an embodiment of the invention, the DNA to be introduced into a mouse preferably, but not exclusively, has a homology of at least 80% to SEQ ID NO:6. The DNA does not necessarily have a homology of at least 80% to SEQ ID NO: 6, as long as it includes a functionally linked enhancer, promoter, and reporter gene, and as long as the enhancer includes at least one AhR-binding enhancer. The mouse to be transfected with the DNA is preferably an inbred line such as C57BL/6, DBA2, or Balb/c.

Besides mice, the animals to be transfected with the DNA may include rats, hamsters, and rabbits. In that case, the aryl hydrocarbon receptor-binding enhancer located 5'-upstream of a tyrosine hydroxylase gene, any promoter, the reporter gene, and the poly(A) addition signal may be selected depending on the species of the animal to be transfected with the DNA, and DNA formed by functionally linking them may be used.

[Introduction of DNA]

The DNA is most generally introduced into an animal by microinjection method. Specifically, a small amount of the DNA including the functionally linked enhancer, promoter, reporter gene, and transcription termination signal sequence is injected under a microscope into the male pronucleus of a fertilized egg at the 1-cell stage using a micromanipulator.

The surviving fertilized egg is transplanted into a pseudopregnant parent oviduct. The mouse with the transplant is then fed, and an individual carrying the introduced DNA is selected from the offspring mice by Southern blotting, PCR and so on. For example, the genome DNA obtained from the tail of each resulting mouse is analyzed by Southern blotting, and the individual mouse inheriting the introduced DNA is selected. This means that the next generation inherits the introduced DNA and supports the production of genetically modified mice useful as animal models.

Other methods include methods using DNA-containing virus vectors and methods using ES cells. The virus vector method may include removing a pellucid zone from an embryo at the 4- to 8-cell stage, infecting the embryo with a virus vector, then developing the embryo into a blastocyst, transferring the blastocyst into a pseudopregnant mother, and developing the blastocyst so that a genetically modified mouse individual can be obtained.

In the method using ES cells (embryonic stem cells), chimeric mice may be produced from DNA-transfected ES cells, and then genetically modified mouse individuals may be obtained.

Homozygous mice having the introduced gene in both homologous chromosomes may be obtained, and the resulting male and female mice may be mated so that genetically modified mice can be reproduced from generation to generation in such a manner that all offspring can stably carry the gene. The fertilized egg for use in maintaining the genetic traits of the genetically modified mouse may be obtained by mating male and female mice. The fertilized egg may also be obtained by natural mating. However, it is preferred that the estrous cycle of female mice be artificially regulated, and then male mice be mated with the female mice.

In an aspect of the invention, there is provided a genetically modified mouse having a central nervous system in which an indicator trait (reporter) is expressed in such a manner that a general-purpose enzyme-activity-detecting reagent kit and a general-purpose measuring apparatus can be used. The use of the genetically modified mouse allows easy and fast in vivo evaluation of the effect of the test substance on the central nervous system. Specifically, the genetically modified mouse according to the invention has the property of expressing the reporter gene in the central nervous system and is useful as a biological testing material for evaluating the effect of the test substance on the central nervous system, because the toxicity of the test substance can be examined by biochemical quantification using the expression of the reporter gene as an indicator.

[Method for Evaluating the Effect of the Test Substance]

An embodiment of the invention is directed to a method that includes administering a test substance to the genetically modified mouse of the invention and then measuring the expression of the reporter gene in the central nervous system of the genetically modified mouse to evaluate the effect of the test substance on the central nervous system.

When the reporter gene is a firefly luciferase gene, the method may include administering luciferin, a substrate for the luciferase, by intraperitoneal injection to the genetically modified mouse 6 to 72 hours after the administration of the test substance to the genetically modified mouse and measuring luminescence derived from the individual or derived from the enzyme activity of the luciferase in the brain with a luminescence measurement system such as an In-Vivo Imaging System (IVIS), manufactured by Xenogen Corporation.

Alternatively, the method may include harvesting the brain from the genetically modified mouse, extracting proteins from the brain with an appropriate protein extraction reagent, adding luciferin to the extract, and then measuring the degree of luminescence derived from the enzyme activity of the luciferase with a commercially available luminometer or the like. In the measurement, when the test substance-administered genetically modified mice significantly differ in the degree of luminescence from the control group genetically modified mice to which no test substance is administered, the test substance is evaluated to have an effect on the central nervous system. At this time, the amount of change in the degree of luminescence caused by the administration of the test substance may be used as an index for determining the magnitude of the effect of the test substance on the central nervous system.

Another embodiment of the invention is directed to a method that includes isolating primary neuronal cells from the genetically modified mouse, exposing the primary neuronal cells to a test substance, and then measuring the expression of the reporter gene in the cells to evaluate the effect of the test substance on the central nervous system. When the reporter gene is a firefly luciferase gene, the method may include isolating primary neuronal cells from the genetically modified mouse, exposing the primary neuronal cells to a test substance, collecting the cells to extract proteins therefrom 2 to 72 hours after the exposure, adding luciferin, a substrate for the luciferase, to the liquid extract, and measuring luminescence derived from the enzyme activity of the luciferase with a luminometer.

In the evaluation, when the primary neuronal cells from the test substance-administered genetically modified mice significantly differ in the degree of luminescence from the primary neuronal cells from the control group genetically modified mice to which no test substance is administered, the test substance is evaluated to have an effect on the central nervous system. At this time, the amount of change in the degree of luminescence caused by the administration of the test substance may be used as an index for determining the magnitude of the effect of the test substance on the central nervous system.

In this context, the "test substance" may be a substance having dioxin-like activity. The inventors have found and already reported that substances having dioxin-like activity can act on the above enhancer region to enhance the activity of the downstream gene. It has been concluded that substances having dioxin-like activity can form a complex with an aryl hydrocarbon receptor, so that the complex can bind to the enhancer region to enhance the activity of the transcription of the downstream gene.

FIG. 1 shows an example of the mechanism of the gene transcription activation by the aryl hydrocarbon receptor (AhR). It is known that dioxins such as TCDD bind to the intracellular AhR to form a complex which binds to a specific sequence of a gene to activate the expression of the downstream gene.

In FIG. 1, Arnt represents an aryl hydrocarbon receptor nuclear translocator. It is known that the AhR that binds to a chemical substance having dioxin-like activity forms a complex with the Arnt, so that the AhR binds to the enhancer to activate the expression of the downstream gene.

According to the invention, the method for determining the harmfulness of a test substance with the genetically modified animal may include bringing the test substance into contact with the genetically modified animal and detecting the expression of the reporter gene.

For example, the contact may be oral administration of the test substance or parenteral administration such as intraperitoneal injection, intravenous injection, intramuscular injection, subcutaneous injection, intracutaneous injection, transvaginal administration, transintestinal administration, transdermal administration, transnasal administration, transpulmonary administration, or instillation, of the test substance. The exposure to the test substance may also be performed by the same method as the contact method.

After the contact, the presence or absence of the expression of the reporter gene or the magnitude thereof may be detected or measured by a method suitable for the expressed reporter gene. In this case, the whole of the animal may be subjected to observation and/or measurement, or the brain may be removed and subjected to a process such as homogenization, cutting, mincing, and/or protein extraction as desired, followed by observation and/or measurement.

Alternatively, the method for determining the harmfulness of a test substance with the genetically modified animal may be performed by bringing a test substance into contact with part of the genetically modified animal. In this case, the test substance may be brought into contact with part of the genetically modified animal, such as a tissue or an organ. Thereafter, the presence or absence of the expression of the reporter gene or the magnitude thereof may be detected or measured by a method suitable for the expressed reporter gene.

While genetically modified mice have been predominantly described as a typical example of the genetically modified animal, animals other than mice may also be transfected with the DNA by known methods in the same manner so that genetically modified animals can be produced, and any of the features described above may also be applied as in the case of mice. In addition, any of such animals may also be used in the method for determining the harmfulness of a test substance as in the case using the mouse.

EXAMPLES

The invention will be more specifically described by the examples below, which are only for illustration and not intended to limit the scope of the invention.

(1) Preparation of Vector to be Introduced into Mouse

A single-stranded DNA was synthesized in which the −175 by to −237 by region located 5'-upstream of the TH gene and containing the sequence shown in SEQ ID NO: 1 was repeated twice (namely, containing two AhR-binding enhancers (SEQ ID NO: 1) for the TH gene). PCR was performed using the DNA as a template and using specific primers so that the single-stranded DNA was converted to a double strand. The single-stranded DNA (SEQ ID NO: 12) and the nucleotide sequences of the specific primers (SEQ ID NO: 13 and NO: 14) are shown below.

```
Single-stranded DNA:
                                          (SEQ ID NO: 12)
5'-GCCAGCCCCTGTCTTCATGTCGTGTCTAGGGCGGAGGGTGATTCAGA

GGCAGTGCCTGCGACAGTGGATGCAGTCTTCATGTCGTGTCTAGGGCGGA

GGGTGATTCAGAGGCAGGTGCCTGCGACAGTGGATGCAATTAGATCT

A-3'

Primer (forward):
                                          (SEQ ID NO: 13)
5'-GCCAGCCCCTGTCTTC-3'

Primer (reverse):
                                          (SEQ ID NO: 14)
5'-TAGATCTAATTGCATC-3'

[SEQ ID NO: 12]
TH gene AHR-binding enhancer (single strand, SEQ
ID NO: 2 x2)
GCCAGCCCCT GTCTTCATGT CGTGTCTAGG GCGGAGGGTG

ATTCAGAGGC AGTGCCTGCG ACAGTGGATG CAGTCTTCAT

GTCGTGTCTA GGGCGGAGGG TGATTCAGAG GCAGGTGCCT

GCGACAGTGG ATGCAATTAG ATCTA
```

-continued

```
                                                   [SEQ ID NO:13]
Primer: TH gene AHR-binding enhancer forward
GCCAGCCCCT GTCTTC

[SEQ ID NO: 14]
Primer: TH gene AHR-binding enhancer reverse
TAGATCTAAT TGCATC
```

The double-stranded DNA obtained by the PCR was phosphorylated with T4 polynucleotide kinase and then ligated with T4 DNA ligase. A DNA fragment having three linked units was separated by agarose gel electrophoresis and then purified using QIAquick Gel Extraction Kit (QIAGEN). The purified DNA fragment included six repeated AhR-binding enhancers. The DNA was incorporated into the vector PGV-P2 (Toyo B-Net Co., LTD.), a luciferase expression vector. First, the SV40 promoter on the PGV-P2 was cut with the restriction enzymes Hind III and Xho I and replaced with a TH gene promoter (the region from the transcription start point (0 bp) to −100 by (5'-upstream) (SEQ ID NO: 4)) so that a recombinant vector (PGV-THp) was prepared. The c-myc tag sequence shown below was then inserted between the Hind III and Nco I sites of the PGV-THp.

```
c-myc tag sequence (forward)
                                                    (SEQ ID NO: 8)
5'-AGCTTATCATGGAGCAGAAACTCATCTCTGAAGAAGATCTGGCCCGGGCGTC-3' c-myc tag sequence (reverse)
                                                    (SEQ ID NO: 9)
5'-GATGGACGCCCGGGCCAGATCTTCTTCAGAGATGAGTTTCTGCTCCATGATA-3'
```

The c-myc tag sequence was obtained by annealing the complementary single-stranded DNAs. In order to facilitate the incorporation into the vector, a Hind III recognition sequence (5'-end) and a Nco I recognition sequence (3'-end) were added to the ends of the c-myc tag. The resulting double-stranded c-myc tag sequence was incorporated between the Hind III and Nco I sites of the PGV-THp. The vector obtained by this process, namely, the vector PGV-THp-Mluc, in which the c-myc tag sequence was added in-frame to the N-terminus of the luciferase gene on the PGV-THp, was cut with Sma I. The DNA sequence (SEQ ID NO: 5) including the six repeated AhR-binding enhancers and the TH gene promoter was inserted into this site so that the vector pTHEn-MLuc to be introduced into mice was prepared.

Figure 2:
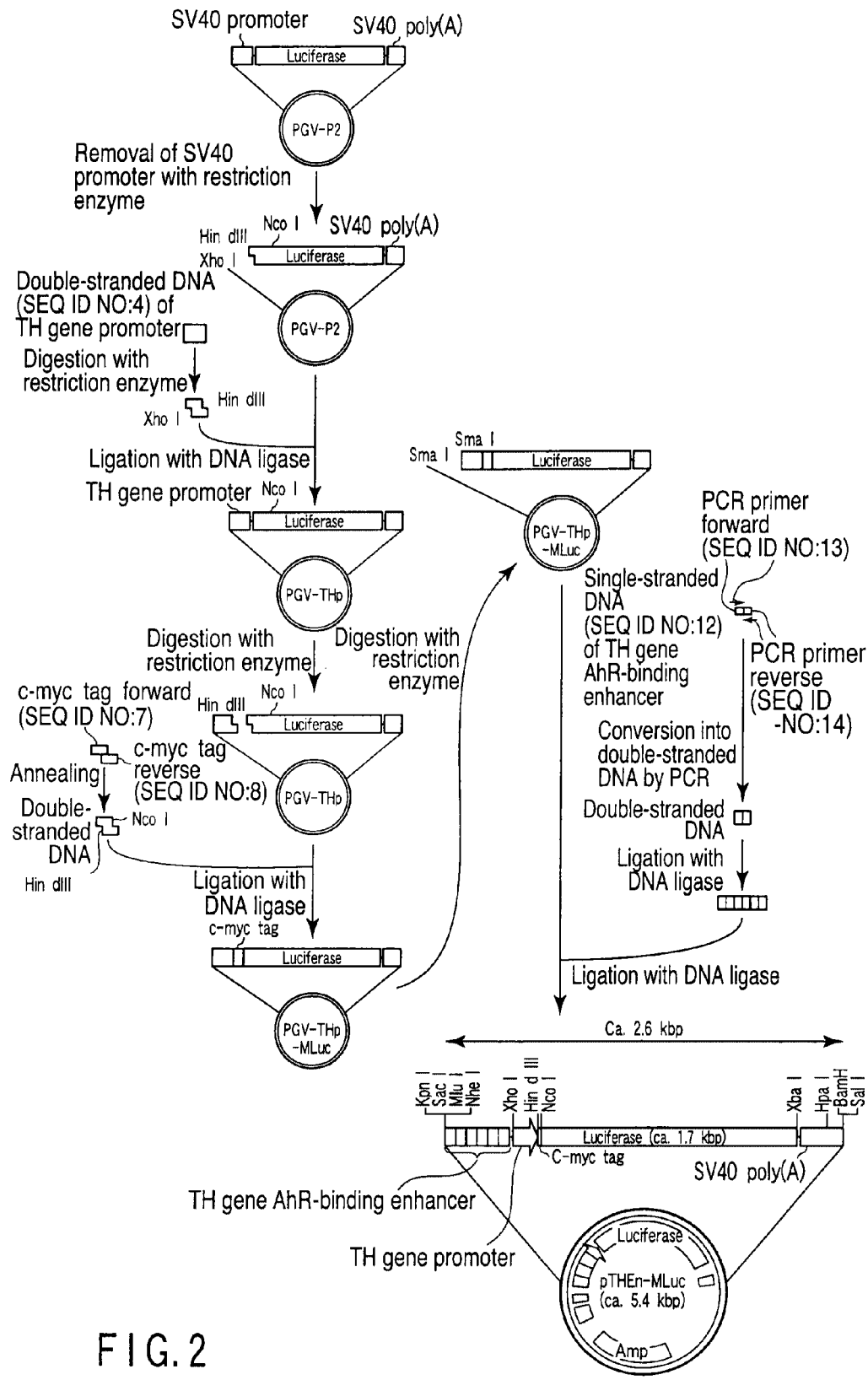
FIG. 2 is a diagram showing a vector preparation flow.

The nucleotide sequence from the AhR-binding enhancer to the c-myc tag sequence on the pTHEn-MLuc was checked by sequencing. The vector preparation flow is shown in FIG. 2.

(2) Production of Genetically Modified Mouse Candidates

C57BL6-strain mice were used. Three days before gene introduction, serum gonadotropin (PMSG) was intraperitoneally injected into 4- to 6-week-old female mice, and chorionic gonadotropin (hCG) was then intraperitoneally injected the day before the gene introduction. After the injection, the female mice were mated with male mice, and the next day, the fallopian tube was removed from female mice having a vaginal plug. The ampulla of the fallopian tube was broken in a hyaluronidase-containing culture solution so that the egg mass was removed. The egg mass was allowed to stand for a while so that fertilized eggs were dissociated from cumulus cells. The fertilized eggs were then collected using an egg collecting pipette. The collected fertilized eggs were washed several times with a culture solution and then cultured in a $CO_2$ incubator.

Figure 3:
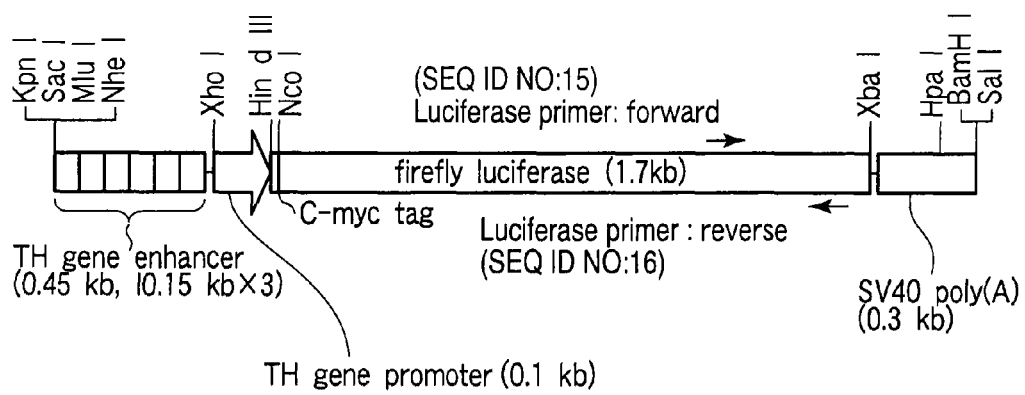
FIG. 3 is a diagram showing DNA to be introduced into a fertilized egg.

The gene to be introduced into the fertilized eggs was prepared by a process including cutting the DNA represented by SEQ ID NO: 6 (see FIG. 3, TH gene enhancer and promoter::c-myc-tagged luciferase gene::SV40 poly(A) signal) from the pTHEn-MLuc with the restriction enzymes Kpn I and Bam HI, purifying the DNA and dissolving the DNA in a TE buffer (10 mM Tris-HCl (pH 7.5), 0.1 mM EDTA) at a concentration of 1 to 2 ng/μl.

The fertilized eggs were taken out of the $CO_2$ incubator and placed in a medium in a chamber mounted on a microscope. The fertilized egg was held with a holding pipette under low magnification, and then the DNA represented by SEQ ID NO: 6 prepared by the method described above was introduced into the fertilized egg with an injection pipette under a high-power differential interference lens. After the medium was replaced, the fertilized eggs after the injection were cultured in the $CO_2$ incubator for 24 hours. The resulting fertilized eggs were transplanted into pseudopregnant female mice and developed so that genetically modified mouse candidates were produced.

(3) Selection of Genetically Modified Mice by Genotyping

Genetically modified mice were selected from the mouse candidates (prepared in the section (2)) using Southern blotting and PCR to detect part of the introduced DNA (SEQ ID NO: 6, the DNA introduced into the fertilized egg) on the genome. An about 2 cm piece was cut from the tail of each mouse (4 to 6 weeks old) and placed in a centrifuge tube. After the cut piece was treated with protease K at 50° C. for 8 to 10 hours, the same amount of a mixture of phenol, chloroform and isoamyl alcohol (25:24:1) was added to the solution and mixed together. The resulting mixture was centrifuged at 15,000 rpm for 3 minutes to be separated into an aqueous layer and a phenol layer. A new tube was attached to the aqueous layer, and ¼ amount of 10 M ammonium acetate and 2.5 times amount of ethanol were added and mixed well. The mixture was then centrifuged at 15,000 rpm for 3 minutes so that the genome DNA was precipitated from the solution and the supernatant was removed. The precipitate was washed with 70% ethanol and then air-dried. The precipitate was dissolved in the TE buffer again so that a mouse genome DNA solution was obtained.

Figure 4:
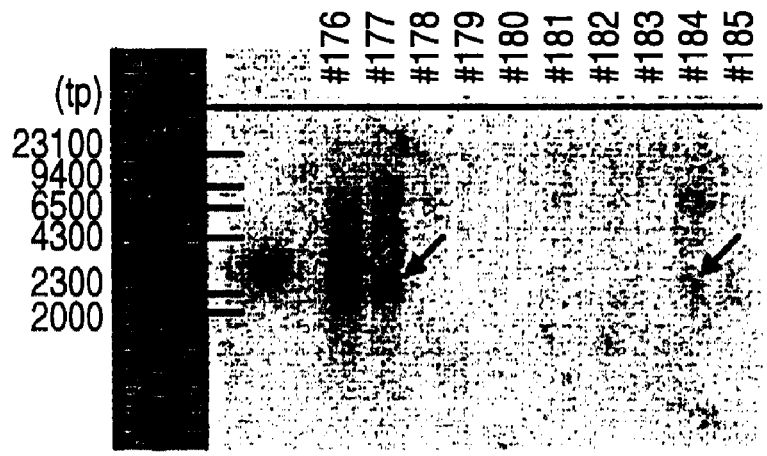
FIG. 4 shows the result of Southern hybridization indicating introduced DNA-derived signals.

The process of genotyping by Southern blotting included adding the restriction enzyme Xho I to the genome DNA solution to completely digest the DNA, subjecting the digest to agarose gel electrophoresis, and then transferring the genome DNA in the gel to a nylon membrane Hybond N$^+$ (GE Healthcare Bioscience) by a capillary transfer method. The DNA was fixed on the membrane by ultraviolet irradiation. The membrane was immersed in a hybridization buffer (¹⁄₂₀ amount of the Denhardt's solution, 50 μg/ml of salmon sperm DNA), and pre-hybridization was performed at 65° C. for 1 hour. Hybridization was then performed at 65° C. overnight in a hybridization buffer containing a radioisotope ($^{32}P$)-labeled probe DNA. The non-specifically adsorbed probe was removed by washing the membrane in washing solution A (2×SSC, 0.1% SDS) at 65° C. for 5 minutes twice and then washing the membrane in washing solution B (0.5×SSC, 0.1% SDS) at 65° C. for 15 minutes twice. A radioisotope ($^{32}$P)-labeled Hind III-Sph I fragment of the pTHEn-MLuc was used as a hybridization probe. The hybridization signals were detected using an X-ray film. As a result, signals derived from the introduced DNA were detected in three genetically modified mouse candidates #176, #177 and #184 (FIG. 4).

The process of genotyping by PCR included determining whether or not part of the luciferase structural gene of the pTHEn-MLuc was amplified using specific primers and using, as a template, the genome DNA extracted from the mouse tail. The nucleotide sequences of the primers used are shown below (SEQ ID NO: 15 and SEQ ID NO: 16).

```
Primer (forward):
                                    (SEQ ID NO: 15)
5'-GCGAAGGTTGTGGATCTGGATACC-3'

Primer (reverse):
                                    (SEQ ID NO: 16)
5'-CCTTTCGGTACTTCGTCCACAAAC-3'

[SEQ ID NO: 15]
Primer: luciferase forward
GCGAAGGTTG TGGATCTGGA TACC

[SEQ ID NO: 16]
Primer: luciferase reverse
CCTTTCGGTA CTTCGTCCAC AAAC
```

Figure 5:
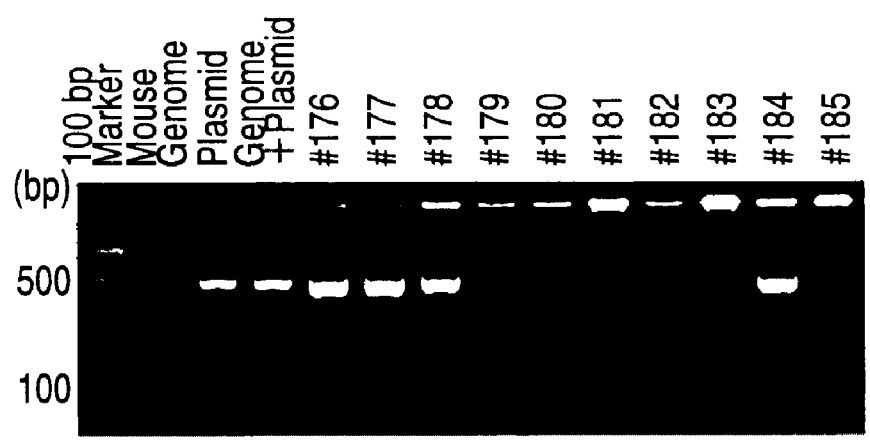
FIG. 5 shows the result of electrophoresis indicating introduced DNA-derived signals.

The amplification was checked by agarose gel electrophoresis. As shown in FIG. 5, signals derived from the introduced DNA were detected in four genetically modified mouse candidates #176, #177, #178, and #184 by PCR genotyping.

The three mice (#176, #177 and #184) in which the introduced DNA signal was detected by both of the two genotyping methods, namely both of the Southern hybridization method and the RCR method, were selected as genetically modified mice and used in the later experiments. Fertilized eggs and sperms from the mouse #176 were cryopreserved and deposited with the International Patent Organism Depositary (Accession No. FERM BP-10993).

(3) Conservation of Genetically Modified Mouse and Line

The three genetically modified mice selected in the section (2) (the 0th generation of the genetically modified mouse, T0 generation) were mated with C57BL/6-strain wild-type mice (back cross) to produce offspring. The offspring of the genetically modified mice were mated with C57BL/6-strain wild-type mice or the offspring of the genetically modified mice so that the genetically modified mice were conserved.

Figure 6:
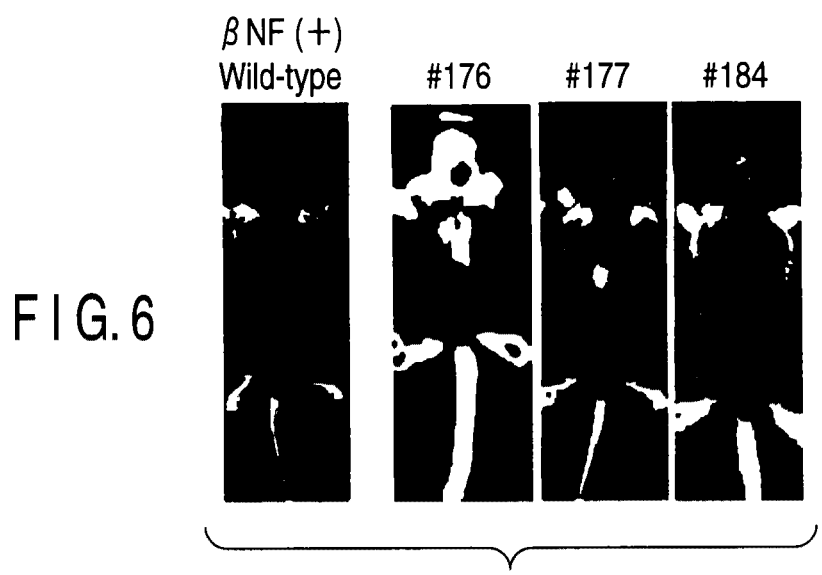
FIG. 6 shows luciferase luminescence in genetically modified mice.
Figure 7:
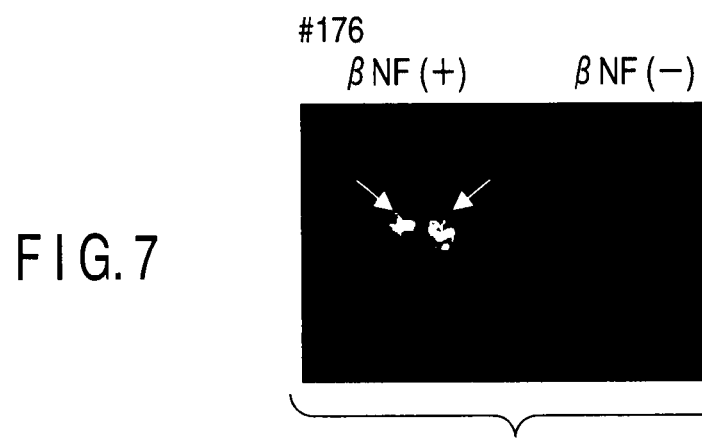
FIG. 7 shows an increase in luminescence in the vicinity of mouse midbrain or hippocampus.

(4) Measurement of Luciferase Luminescence in Genetically Modified Mouse During Exposure to βNF A dioxin analog, β-naphthoflavone (βNF), was used as a test substance. A solution of βNF in corn oil was intraperitoneally injected at a βNF dose of 40 mg/kg into each of the genetically modified mice #176 (4 weeks old), #177 (6 weeks old) and #184 (6 weeks old) in the T1 generation. The same amount of corn oil as the amount of the solution in the βNF-administered group was intraperitoneally administered to each of the control group mice (the genetically modified mice in the T1 generation). A luciferin solution was intraperitoneally administered at a dose of 150 mg/kg BW to these mice 72 hours after the above administration. After 5 minutes, an In-Vivo Imaging System (IVIS 100-series), manufactured by Xenogen Corporation, was used to detect luciferase luminescence in the mice. As a result, luciferase luminescence was observed in all the genetically modified mice (FIG. 6). In addition, the brain of the genetically modified mouse #176 was cut in the vicinity of the midbrain, and luminescence from the cut section was measured with the IVIS System. As a result, an increase in the degree of luminescence was detected in the vicinity of the midbrain or hippocampus of the βNF-administered mouse (FIG. 7). The results showed that when the change in the expression of the reporter gene was used as an indicator, the genetically modified mice (#176, #177 and #184) made it possible to evaluate the effect of βNF on the central nervous system.

(5) Measurement of Luciferase Luminescence in Primary Neuronal Cells Isolated from Genetically Modified Mouse During Exposure to Dioxin (TCDD)

Figure 8:
FIG. 8 shows cultured nerve cells.

The genetically modified mouse #176 (hetero, male) was mated with a wild-type mouse, and 12 days after the observation of the plug, the brain was removed from the embryo (E12: an embryonic age of 12 days) under a sterile environment. All the removed embryonic brains were collected, and 0.25% trypsin was added thereto and incubated at 37° C. for 15 minutes. The trypsin was removed. After washed tree times with the Hank's solution, the cells were suspended in a serum-containing DF 1:1 medium (Dulbecco-F12 equal-ratio mixture medium+10% fetal bovine serum). The suspension was inoculated on a culture plate (coated with ornithine-fibronectin) and cultured under a 37° C./5% $CO_2$ atmosphere. After culturing overnight, the medium was replaced with a serum-free medium (Dulbecco MEM/Ham's F12 equal-ratio mixture medium+TIPS (transferrin/insulin/penicillin/streptomycin)) so that the neuronal cells could be predominantly grown (FIG. 8).

After 4 days, TCDD (2,3,7,8-tetrachlorodibenzo-p-dioxin, Kanto Kagaku) was added at a final concentration of 0, 0.1 or 10 ng/ml to the medium, and after 24 hours, the cells were collected. After the collected cells were washed twice with a phosphate buffer solution, 200 μl of a protein extraction solution (Toyo B-Net Co., Ltd.) was added thereto and stirred at room temperature for 15 minutes. The cells were then broken by freezing (−80° C.) and thawing (room temperature). The broken cell solution was collected in a 1.5 ml tube and then centrifuged so that the supernatant was collected as an extracted protein solution. The resulting extracted protein solution was used in the measurement of luciferase luminescence. In the luciferase luminescence measurement, 100 μl of an assay solution (PicaGene Assay Kit, Toyo B-Net Co., Ltd.) was added to 10 μl of the collected protein solution and stirred, and immediately after the stirring, the degree of luminescence per 2 minutes was measured with a luminometer LB-940 (Berthold). The resulting degree of luminescence was divided by the total protein amount of the protein solution so that it was converted into a relative luminescence intensity (RLU/min/μg protein). The total protein amount of the solution was measured with a protein assay kit (Bio-Rad). As a result, the primary neuronal cells isolated from the genetically modified mouse showed a TCDD concentration-dependent increase in the degree of luminescence (for example, the exposure to 0.1 nM TCDD and 10 nM TCDD produced a 1.3 times increase and a 3.1 times increase from the unexposed case, respectively; FIG. 9). The result showed that when the change in the expression of the reporter gene was used as an indicator, the primary neuronal cells isolated from the genetically modified mouse (#176) made it possible to evaluate the effect of TCDD on the central nervous system.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A transgenic animal selected from the group consisting of a mouse, a rat, a hamster, and a rabbit, whose genome comprises a heterologous DNA comprising an aryl hydrocarbon receptor-binding enhancer operably linked to a promoter, a reporter gene, and a poly(A) addition signal; wherein the aryl hydrocarbon receptor-binding enhancer comprises the polynucleotide sequence of SEQ ID NO: 3.

2. The transgenic animal according to claim 1, which is a mouse.

3. The transgenic animal according to claim 2, wherein the promoter consists of SEQ ID NO: 4.

4. The transgenic animal according to claim 2, wherein the polynucleotide sequence of the enhancer and the promoter linked together consists of the polynucleotide sequence of SEQ ID NO: 5.

5. The transgenic animal according to claim 2, wherein the heterologous DNA comprising an aryl hydrocarbon receptor-binding enhancer operably linked to a promoter, a reporter gene, and a poly(A) addition signal consists of SEQ ID NO: 6.

6. The transgenic animal according to claim 5, having Accession No. FERM BP-10993.

7. The transgenic animal according to claim 1, which is a rat.

8. The transgenic animal according to claim 1, wherein the reporter gene is selected from the group consisting of a luciferase gene, a green fluorescent protein gene, a β-galactosidase gene, and a chloramphenicol acetyltransferase gene.

9. The transgenic animal according to claim 8, wherein the reporter gene is a luciferase gene.

10. The transgenic animal according to claim 1, wherein expression of the reporter gene is induced in a central nervous system.

11. A method for determining harmfulness of a test substance, comprising:
   bringing the test substance into contact with the transgenic animal according to claim 1 or part thereof; and
   detecting expression of a reporter gene.

12. A method for determining harmfulness of a test substance, comprising:
   bringing the test substance into contact with the transgenic animal according to claim 9 or part thereof; and
   detecting expression of a luciferase gene.

13. A method for detecting an effect of a test substance on a dopamine synthesis, comprising bringing the test substance into contact with the transgenic animal according to claim 1 or part thereof
   detecting expression of a luciferase gene.

14. A method for determining an effect of a test substance on a dopamine synthesis, comprising:
   bringing the test substance into contact with the transgenic animal according to claim 9 or part thereof; and
   detecting test substance-induced expression of a luciferase gene.

* * * * *